United States Patent [19]

Seto et al.

[11] Patent Number: 4,900,752

[45] Date of Patent: Feb. 13, 1990

[54] PYRANOBENZOXADIAZOLE DERIVATIVES

[75] Inventors: Kiyotomo Seto; Hiroo Matsumoto; Yoshimasa Kamikawaji; Kazuhiko Ohrai; Kyoko Nakayama; Ryozo Sakoda, all of Funabashi; Yukinori Masuda, Saitama, all of Japan

[73] Assignee: Nissan Chemical Industries, Ltd., Tokyo, Japan

[21] Appl. No.: 304,641

[22] Filed: Feb. 1, 1989

[30] Foreign Application Priority Data

Feb. 3, 1988 [JP] Japan .................................. 63-23409
Mar. 1, 1988 [JP] Japan .................................. 63-48458
Mar. 29, 1988 [JP] Japan .................................. 63-75762
May 25, 1988 [JP] Japan .................................. 63-127584

[51] Int. Cl.$^4$ .................... C07D 498/04; A64K 31/41
[52] U.S. Cl. .................................. 514/364; 544/238; 546/197; 548/126
[58] Field of Search .................. 548/126; 514/364; 546/199

[56] References Cited

U.S. PATENT DOCUMENTS

4,470,135  10/1984  Neuman ............................... 548/128

FOREIGN PATENT DOCUMENTS

| 0028064 | 5/1981 | European Pat. Off. | 514/364 |
| 0028449 | 5/1981 | European Pat. Off. | 514/364 |
| 0033612 | 8/1981 | European Pat. Off. | 514/364 |
| 1406106 | 6/1965 | France | 548/161 |
| 5867683 | 4/1983 | Japan | 514/364 |
| 025238 | 9/1981 | Switzerland | 548/161 |

OTHER PUBLICATIONS

T. C. Hamilton, Sheila W. Weir & A. H. Weston, Br. J. Pharmac (1986), 88, pp. 103–111, Comparison of the effects of BRL 34915 and verapamil on electrical and mechanical activity in rat portal vein.—Beecham Pharma., Research Div.,—University of Manchester.
S. L. Allen, J. P. Boyle, J. Cortijo, R. W. Foster, G. P. Moran & R. C. Small, Br. J. Pharmac. (1986) 89, pp. 395–405, Electrical and mechanical effects of BRL34915 in guinea-pig isolated trachealis-Smooth Muscle Research Grp., Dept of Pharmacology—University of Manchester.
K Channel Blocker Supersensitivity—pp. 425–431.
M. Hollingsworth, T. Amedee, Diane Edwards, J. Mironneau, J. P. Savineau, R. C. Small & A. H. Weston, The relaxant action of BRL 34915 in rat uterus, Br. J. Pharmac (1987). 91, pp. 803–813,—Smooth Muscle Research Group, Dept. of Physiological Sciences, University of Manchester.
Drug License Opportunities IMS World Publications Ltd., News Round Up, 9/7/87, No. 312.

*Primary Examiner*—Robert Gerstl
*Attorney, Agent, or Firm*—Oliff & Berridge

[57] ABSTRACT

A compounds of the formula (I):

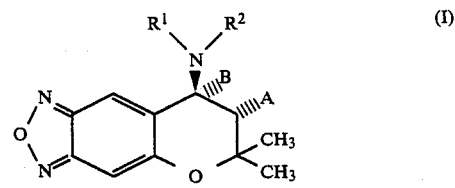

wherein A represents OH or $OC(O)CH_{3-n}X_n$, B represents hydrogen atom, or A and B together represent a bond; $R^1$ represents hydrogen atom, $R^2$ represents hydrogen atom, $C(Z)CH_{3-n}X_n$ or $C(Z)NHCH_{3-n}X_n$ or $R^1$ and $R^2$ together represent $(CH_2)_m$, $(CH_2)_{m-1}C(Z)$, $N(R^3)(CH_2)_2C(Z)$, $(CH_2)_{m-2}NHC(Z)$ or $(CH_2)_{m-2}OC(Z)$ in which X represents fluorine atom, chlorine atom, bromine atom, a methyl group or a methoxy group and n represents 0 or an integer of 1 to 3, Z represents oxygem atom or sulfur atom, m represents an integer of 4 or 5 and $R^3$ represents hydrogen atom or a methyl group, and pharmacological acceptable salts of the compounds which can form salts, processes therefor and pharmaceutical use of the compounds.

15 Claims, No Drawings

PYRANOBENZOXADIAZOLE DERIVATIVES

BACKGROUND OF THE INVENTION

1. Field of the Invention

The present invention relates to novel pyranobenzoxadiazole derivatives, pharmaceutical compositions containing said derivatives, use thereof for the therapy of hypertension or asthma which causes in mammarian animals inclusive of human being and a process for producing the above.

2. Description of the Prior Art

Japanese Patent Laid-open Publication No. Sho 58-67683 (67683/1983) discloses that a compound (Development code No. BRL-34915) of the formula (A):

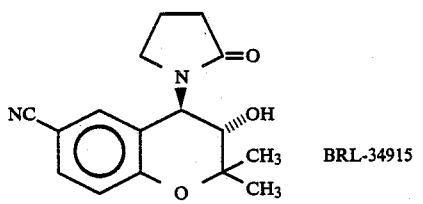

(A)

BRL-34915 has an activity for lowering blood pressure with respect to spontaneously hypertensive rats.

Br. J. Pharmac. (1986), 88, p.p. 103–111 discloses the possibility that the compound BRL-34915 activates $K^+$ channel and moves resting potential of membrane to the hyper polarization.

Br. J. Pharmac. (1986), 89, p.p. 395–405 shows that the compound BRL-34915 loosens trachealis of guinea pig and suggests that it has utility as a medicine for the therapy of asthma.

Angiology (1987), 27, pp. 425–431 suggests that a composition for activating $K^+$ channel is effective for the treatment of arrhythmia and angina pectoris.

Br. J. Pharmac. (1987), 91, pp. 803–813 shows that the compound BRL-34915 loosens uterus of rats. For this fact, it may be effective for preventing premature delivery.

DLO News ROUND-UP No. 312 (1987) shows that the compound BRL-34915 is effective for the medical treatment of incontinence and pain.

However, EP-A-28449 and EP-A-28064 shows that the benzopyran derivatives to which the BRL-34915 belongs may undesirably affect the action of the heart.

As the result of the intensive research of novel compounds, therefore, the present inventors have found out that novel pyranobenzoxadiazole derivatives have strong activity for lowering blood pressure. Then, the present inventors have accomplished the present invention.

SUMMARY OF THE INVENTIO

The object of the present invention is to provide novel pyranobenzoxadiazole derivatives.

Another object of the present invention is to provide processes for producing the derivatives.

Still another object of the present invention is to provide antihypertensive, coronary or cerebral vasodilator or anti-asthma compositions containing as an active ingredient said derivatives.

Still another object of the present invention is to provide methods for treating hypertension, cardiovascular disorder, cerebrovascular disorder and asthma.

DETAILED DESCRIPTION OF THE INVENTION

The novel pyranobenzoxadiazole derivatives of the present invention are represented by the formula (I):

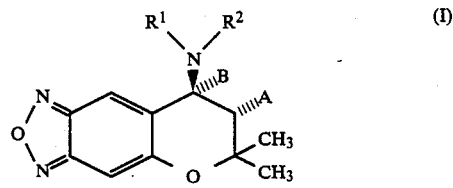

(I)

wherein A represents OH or $OC(O)CH_{3-n}X_n$ in which X represents fluorine atom, chlorine atom, bromine atom, a methyl group or a methoxy group and n represents 0 or an integer of 1 to 3, or A and B together represent a bond;

B represents hydrogen atom or a bond together with A;

when $R^1$ represents hydrogen atom, $R^2$ represents hydrogen atom, $C(Z)CH_{3-n}X_n$ or $C(Z)NHCH_{3-n}X_n$ in which Z represents oxygen atom or sulfur atom;

when $R^1$ does not represent hydrogen atom, $R^1$ and $R^2$ together represent $(CH_2)_m$, $(CH_2)_{m-1}C(Z)$, $N(R^3)(CH_2)_2C(Z)$, $(CH_2)_{m-2}NHC(Z)$ or $(CH_2)_{m-2}OC(Z)$ in which m represents an integer of 4 or 5 and $R^3$ represents hydrogen atom or a methyl group, except for the compound in which $R^1$ and $R^2$ simulatenously represent hydrogen atom and A represents OH, and the pharmacological acceptable salts of the compounds which can form salts have strong activity for lowering blood pressure.

The compounds of the formula (I) are novel compounds and the fact that these compounds except for the compound in which $R^1$ and $R^2$ simulatenously represent hydrogen atom and A represents OH have strong activity for lowering blood pressure has not expected so far at all.

Although stereoisomer or optical isomer is contained in the compounds of the formula (I), the present invention contains all of these isomers.

Each of substituents in the formula (I) representing the compounds having an activity for lowering blood pressure is explained in detail.

A may be, for example, OH, $OC(O)CH_3$, $OC(O)CH_2F$, $OC(O)CH_2Cl$, $OC(O)CH_2Br$, $OC(O)CF_3$, $OC(O)CH_2OCH_3$ or $OC(O)CH_2CH_3$.

A may represent a bond together with B.

The preferable example of A is OH.

When $R^1$ represents hydrogen atom, $R^2$ may be, for example, hydrogen atom, $C(O)CH_3$, $C(O)CH_2F$, $C(O)CH_2Cl$, $C(O)CH_2Br$, $C(O)CF_3$, $OC(O)CH_2OCH_3$, $C(O)CH_2CH_3$, $C(O)NHCH_3$, $C(O)NHCH_2CH_3$, $C(S)CH_3$ and $C(S)NHCH_3$, in which $C(O)CH_3$, $C(O)CH_2F$ and $C(O)NHCH_3$ are preferable.

When $R^1$ does not represent hydrogen atom, $R^1$ and $R^2$ together represent $(CH_2)_4$, $(CH_2)_5$, $(CH_2)_3C(O)$, $(CH_2)_4C(O)$, $NH(CH_2)_2C(O)$, $N(CH_3)(CH_2)_2C(O)$, $(CH_2)_2NHC(O)$ and $(CH_2)_2OC(O)$, in which $(CH_2)_4$, $(CH_2)_5$, $(CH_2)_3C(O)$, $(CH_2)_4C(O)$, $NH(CH_2)_2C(0)$ and $N(CH_3)(CH_2)_2C(O)$ are preferable.

The following is the explanation of the method for synthesizing the compounds of the formula (I).

Reaction Scheme 1

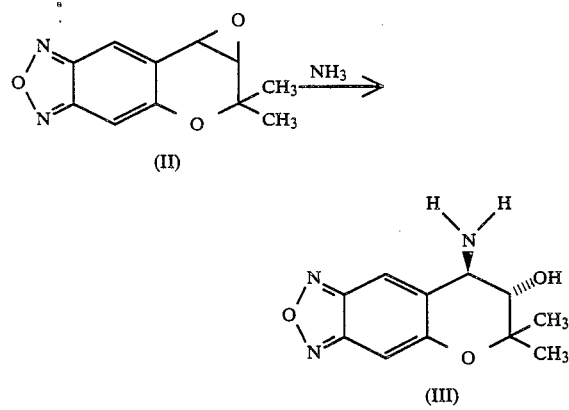

The compound of the formula (II) is reacted with ammonia in an inert solvent to obtain the compound of the formula (III). The preferable solvents may be methanol, ethanol and isopropanol. The reaction temperature may be within the range of from 0° C. to 90° C., and preferably within the range of from 15° C. to 60° C. If desired and necessary, the reaction may be conducted under the pressure. The molar ratio of the reaction may be 1 to excess mole of ammonia with respect to the compound of the formula (II), 2 to 5-time moles being preferable.

Reaction Scheme 2

$$(III) \xrightarrow{YC(O)CH_{3-n}X_n / -HY} (IV)$$

Reaction Scheme 3

$$(III) \xrightarrow{C(O)NCH_{3-n}X_n / (catalyst)} (V)$$

Reaction Scheme 4

$$(II) \xrightarrow{(CH_2)_m \atop NH} (VI)$$

Reaction Scheme 5

$$(III) \xrightarrow{(1)\ YC(O)(CH_2)_{m-1}Y^1 / -HY} \xrightarrow{(2)\ -HY^1} (VII)$$

Reaction Scheme 6

-continued

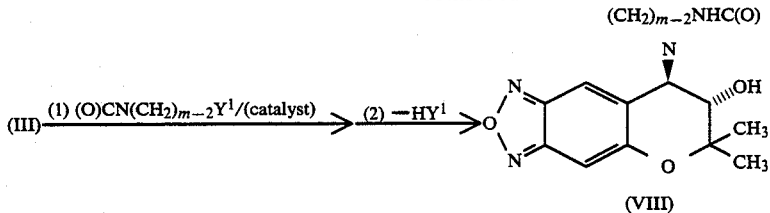

(VIII)

Reaction Scheme 7

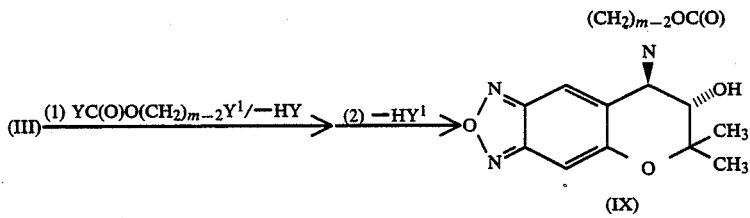

(IX)

Reaction Scheme 8

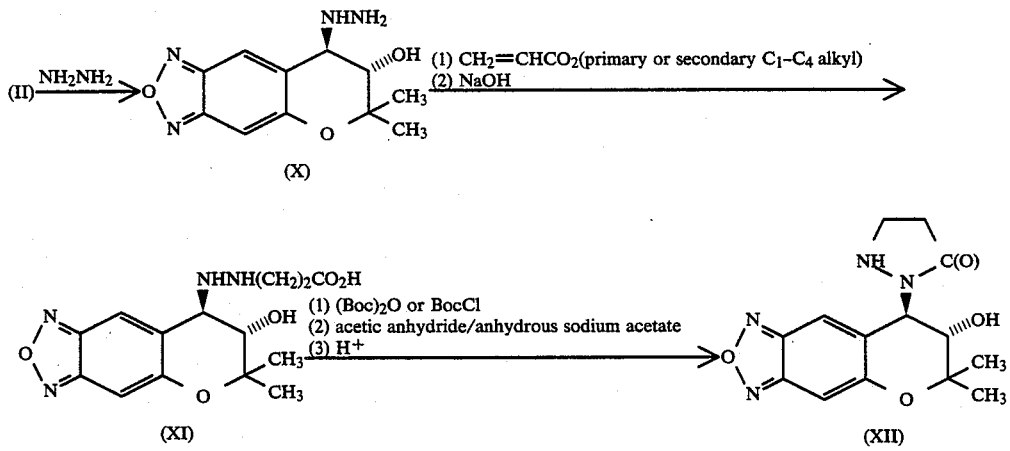

In the Reaction Schems, Y represents conventional leaving group such as halogen atom (chlorine atom, bromine atom or iodine atom), acetoxy or trifluoroacetoxy. Y' represents chlorine atom, bromine atom, iodine atom, o-toluensulfonate, p-toluensulfonate or methanesulfonate. The m, n and X have the same meanings as defined in the formula (I).

In the formula (I), the compounds (compounds of the formula (IV) or (V)) in which $R^1$ represents hydrogen atom may be synthesized by the processes shown by the Reaction Schemes 2 and 3.

That is, the compounds of the formula (III) are reacted with $YC(O)CH_{3-n}X_n$ to obtain the compounds of the formula (IV). (see the Reaction Scheme 2)

The molar ratio of $YC(O)CH_{3-n}X_n$ with respect to the compounds of the formula (III) is from 1.0 to 1.5-time moles, preferably from 1.01 to 1.05-time moles.

The reaction solvent is an inert solvent and is, for example, halogenated alkane solvents such as dichloromethane, chloroform or carbon tetrachloride, benzene, toluene, ethyl ether or n-hexane.

The examples of the acid trapping agent are tert-amine such as triethylamine and pyridine, potassium carbonate and sodium carbonate. The molar ratio of these substances may be excessive with respect to $YC(O)CH_{3-n}X_n$, preferably 1.0 to 2.0 times.

The reaction temperature is from 0° to 90° C., preferably from 0° to 30° C.

The reaction time may be enough when the acylation can be sufficiently proceeded. It is 0.5 to 20 hours, preferably 1 to 2 hours.

The compounds of the formula (III) is reacted with $C(O)NCH_{3-n}X_n$ to obtain the compounds of the formula (V). (see the Reaction Scheme 3)

The molar ratio of $C(O)NCH_{3-n}X_n$ with respect to the compounds of the formula (III) is from 1.01 to 1.5-time moles, preferably from 1.01 to 1.05-time moles.

The solvents are the same as those in the Reaction Scheme 2.

Catalyst may be used for accelating the reaction. Examples of the catalyst to be used are triethylamine and trimethylamine. The molar ratio of these substances is from 0.01 to 0.05-time moles with respect to the compounds of the formula (III).

The reaction temperature is from 0° to 90° C., preferably from 5° to 30° C.

As the reaction time, such time may be enough that the acylating raction can be sufficiently proceeded. It is from 0.5 to 20 hours, preferably from 1 to 2 hours.

In case that $R^1$ and $R^2$ together represent $(CH_2)_m$, in accordance with the process of the Reaction Scheme 4, the compounds of the formula (II) are reacted with pyrrolidine or piperidine to synthesize the compounds of the formula (VI).

The reaction conditions are the same as those of the above Reaction Scheme 1.

The compounds of the formula (I) in which $R^1$ and $R^2$ together represent $(CH_2)_{m-1}C(O)$, $(CH_2)_{m-2}NHC(O)$ and $(CH_2)_{m-2}OC(O)$ are synthesized by the Reaction Schemes 5, 6 and 7, respectively.

That is, the compounds of the formula (III) are respectively reacted with $YC(O)(CH_2)_{m-1}Y^1$, $Y^1(CH_2)_{m-2}NC(O)$ or $YC(O)O(CH_2)_{m-2}Y^1$ and then, the obtained compounds carried out under cyclization reaction by elimination reaction of $HY^1$ in accordance with conventional methods commonly employed to synthesize the respective compounds of the formulae (VII), (VIII) and (IX).

The reaction conditions are the same as those of the Reaction Scheme 2 in case that the compounds of the formula (III) are reacted with acid chloride. The reaction conditions are the same as those of the Reaction Scheme 3 in case that the compounds of the formula (III) are reacted with isocyanates.

In these reactions, cyclization reaction is conducted by the deacidification reaction after acylation reaction to amino group is completed. The solvents in the cyclization reaction are the same as those of the Reaction Scheme 2.

As acid trapping agent, potassium carbonate, sodium carbonate, potassium bicarbonate and sodium bicarbonate may be used. The molar ratio thereof is excess times with respect to the compounds of the formula (III), preferably from 1.5 to 3.0-time moles.

The reaction temperature of the cyclization reaction is from 0° C. to the reflux temperature of a reaction solution of the cyclization reaction, preferably from 30° C. to the reflux temperature of the reaction solution.

The reaction time is from 0.5 to 24 hours, preferably from 0.5 to 5 hours.

The compounds of the formula (I) in which $R^1$ and $R^2$ together represent $NH(CH_2)_{m-2}C(O)$ may be synthesized by the method shown by the Reaction Scheme 8.

Hydrazine which is reacted to the compounds of the formula (II) may be either of anhydrous hydrzaine or hydrated hydrazine.

The molar ratio of hydrazine with respect to the compounds of the formula (II) are from 1.01 to 3.0-time moles, preferably from 1.01 to 1.05-time moles.

The solvents are alcohol solvents such as methanonl, ethanol and isopropanol.

The reaction temperature is from 0° to 100° C., preferably 0° to 60° C.

As the reaction time, such time may be enough that the reaction can be sufficiently proceeded. In general, it may be from 10 minutes to 10 hours, preferably 0.5 to 2 hours.

The molar ratio of primary or secondary $C_1$-$C_2$ alkyl (lower alkyl) acrylate which is reacted with the compounds of the formula (X) which are obtained by reacting hydrazine to the compounds of the formula (II) is from 0.7 to 1.0-time moles. The solvent used for this reaction is methanol, ethanol or isopropanol and the like.

The reaction temperature is from 0° to 150° C., preferably from 15° C. to the reflux temperature of the solvent.

As the reaction time, such time may be enough that the reaction can be sufficiently proceeded. In general, it may be from 0.5 to 20 hours, preferably from 2 to 3 hours.

The lower alkyl ester of thus obtained compounds of the formula (XI) is reacted with sodium hydroxide or potassium hydroxide to synthesize the compounds of the formula (XI).

The molar ratio of the sodium hydroxide or potassium hydroxide used above with respect to the alkyl ester as the raw material is from 1.0 to 1.5-time moles, preferably from 1.0 to 1.05-time moles.

The solvents which are used for the hydrolysis of the lower alkyl ester are alcohol solvents such as methanol, ethanol and isopropanol.

The reaction temperature is from 0° to 100° C., preferably from 15° to 30° C.

The reaction time is from 1 to 20 hours, preferably from 2 to 3 hours.

The obtained compounds of the formula (XI) is first reacted with di-tert-butyl dicarbonate or tert-butyloxycarbonyl chloride, and amino groups (corresponds to a part of hydrazine group) adjacent to methylene chain in the compound (XI) is protected by tert-butoxy carbonyl group. The molar ratio of di-tert-butyl carbonate or tert-butyloxycarbonyl chloride with respect to the compounds of the formula (XI) is from 1.0 to 1.05-time moles.

The solvents to be used are inert solvents such as dichloromethane, chloroform, tetrahydrofuran (THF) and ethyl ether. The catalysts to be used in the reaction are basic catalysts such as triethylamine, trimethylamine, DBU (1,8-Diazabicyclo [5.4.0] undec-7-ene) and pyridine.

The reaction temperature is from 0° to 150° C., preferably 10° to 30° C.

The reaction time is from 0.5 to 20 hours, preferably 1 to 2 hours.

After the introduction of the protecting group, the protected compound was subjected to cyclization reaction in the presence of acetic anhydride and sodium acetate.

The acetic anhydride as a cyclization reagent can be also used as a solvent. The amount of the sodium acetate is from 0.1 to 3-time equivalent with respect to the acetic anhydride to be used, preferably 0.1 to 0.3-time equivalent.

Next, the compounds of the formula (XII) can be obtained by eliminating the protecting group (tert-butyloxy carbonyl group) from the compounds mentioned above.

The deprotection is conducted by the addition of an acid such as trifluoroacetic acid. The other acids are p-toluene sulfonic and sulfuric acid.

The acid is generally used in an amount of excess mol with respect to the compound subjected to the deprotection, i.e., from 1.5 to 10-time moles, preferably 1.5 to 5-time moles.

The reaction temperature is from 0° to 30° C., preferably 0° to 15° C.

The reaction time is from 0.5 to 10 hours, preferably 0.5 to 3 hours.

The compounds of the formula (I) in which $R^1$ and $R^2$ together represent $N(CH_3)(CH_2)_{m-2}C(O)$ may be synthesized by methylating the compounds of the formulae (XI) or (XII) with methylating agent commonly employed, e.g., methyl iodide and dimethyl sulfate in the presence of acid trapping agent.

In the above, the case that Z represents oxygen atom is explained. In case that Z represents sulfur atom, the intended compounds may be obtained by sulfurating the respectively corresponding compounds with Lowesson's reagent. Furthermore, the compounds of the formulae (V) or (VIII) in which Z represents sulfur atom may be obtained by reacting the compounds of the formula (III) with $X_nCH_{3-n}NC(C)$ or $Y^1(CH_2)_{m-2}NC(S)$, respectively.

The compounds represented by the formula (I) in which A and B together represent a bond may be readily obtained by treating the compounds of the formula (I) in which A represents OH and B represents hydrogen atom with alkali such as sodium hydride, sodium hydroxide and sodium carbonate in an inert solvent such as THF, dimethylformamide (DMF) and chloroform.

In this case, the isolation of the compounds of the formula (I) in which A represents OH and B represents hydrogen atom is not necessarily required.

The compounds of the formula (II) which are raw material may be synthesized in accordance with the following reaction scheme

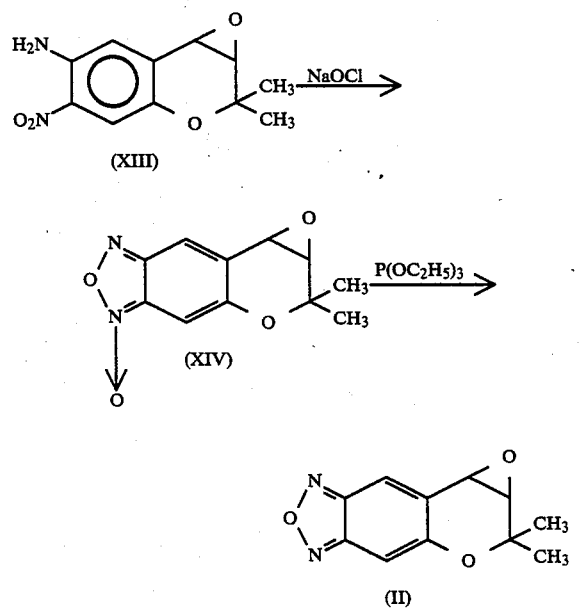

After the known compounds of the formula (XIII) are treated by sodium hypochlorite to obtain the compounds of the formula (XIV), the compounds of the formula (II) may be obtained by reducing N-oxide group with reducing agent such as triethyl phosphite and sodium azide. By reducing N-oxide group of the compounds of the formula (XV) which are obtained by epoxy cyclization reaction of the compounds of the formula (XIV) with ammonia, pyrrolidine or piperidine, with suitable reducing agent such as triethyl phosphite and sodium azide, the compound of the formula (XV) can be introduced into the compounds of the formula (I-2). However, it is preferable to carry out the reaction of the compounds (II) with amines.

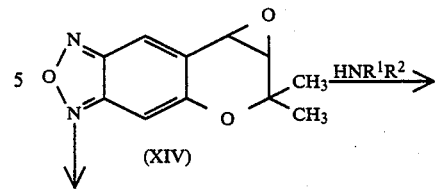

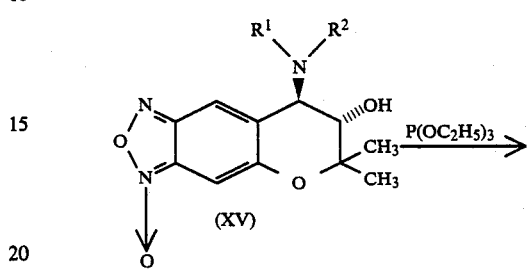

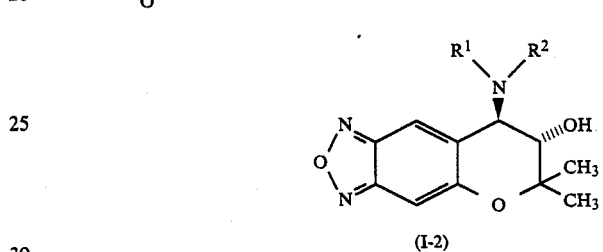

As described above, the present inventors have found out that the active compounds of the present invention (hereinafter referred to as the present compounds) except for the compound in which $R^1$ and $R^2$ simultaneously represent hydrogen atom and A represents OH, have strong vasolidating activity and activity for lowering blood pressure. Accordingly, the present compounds are considered to be useful as a medicament in the therapy of hypertension, angina pectoris, arrhythmia, cerebrovascular disorder and asthma of mammals inclusive of human being. Therefore, the present invention provides pharmaceutical compositions containing effective amount of the present compounds for the theraphy of the above-mentioned diseases.

As the manner of administration of the present compounds, there may be mentioned a parenteral administration by injection (subcutaneous, intravenous, intramuscular or intraperitoneal injection), an ointment, a suppository or an aerosol, or an oral administration in the form of tablets, capsules, granules, pills, sirups, liquids, emulsions or suspensions.

The above pharmacological or veterinary composition contains the present compounds in an amount of from 0.1 to about 99.5% by weight, preferably from about 0.5 to 95% by weight, based on the total weight of the composition. To the present compounds or to the composition containing the present compounds, other pharmacologically or veterinarily active compounds may be incorporated. Further, the composition of the present invention may contain a plurality of the present compounds.

The clinical dose of the present compounds varies depending upon the age, the body weight, the sensitivity or the symptom, etc. of the patient. However, the effective daily dose is usually from 0.1 to 100 mg, preferably from 0.5 to 10 mg, for an adult. However, if necessary, an amount outside the above range may be employed.

The present compounds may be formulated into various suitable formulations depending upon the manner of administration, in accordance with conventional methods commonly employed for the preparation of pharmaceutical formulations.

Namely, tablets, capsules, granules or pills for oral administration, may be prepared by using an excipient such as sugar, lactose, glucose, starch or mannitol; a binder such as hydroxypropyl cellulose, sirups, gum arabic, gelatin, sorbitol, tragacanth gum, methyl cellulose or polyvinylpyrrolidone; a disintegrant such as starch, carboxymethyl cellulose or its calcium salt, crystal cellulose powder or polyethylene glycol; a lubricant such as talc, magnesium or calcium stearate, colloidal silica, sodium laurate or glycerol.

The injections, solutions, emulsions, suspensions, sirups or aerosols, may be prepared by using a solvent for the active ingredient such as water, ethyl alcohol, isopropyl alcohol, propylene glycol, 1,3-butylene glycol, or polyethylene glycol; a surfactant such as a sorbitol fatty acid ester, a polyoxyethylene sorbitol fatty acid ester, a polyoxyethylene fatty acid ester, a polyoxyethylene ether of hydrogenated caster oil or lecithin; a suspending agent such as a sodium salt of carboxymethyl, a cellulose derivative such as methyl cellulose, or a natural rubber such as tragacanth gum or gum arabic; or a preservative such as a paraoxy benzoic acid, benzalkonium chloride or a salt of sorbic acid. Likewise, ointments may be prepared by using, e.g., white vaseline, liquid paraffin, a higher alcohol, Macrogol ointment, hydro-philic ointment or hydro-gel base. The suppositories may be prepared by using, e.g., cocoa butter, polyethylene glycol, lanolin, fatty acid triglyceride, coconut oil or polysorbate.

(TEST EXAMPLES)

Antihypertensive effect

The test compounds were dissolved or suspended in the solvent (PEG400*:H$_2$O=3:1(v/v)) and administered to male spontaneously hypertensive rats (SHR, 11 weeks) via an oral route.
(*: polyethylene glycol of molecular weight range 380-420)

Systolic blood pressure (SBP) was measured by a tailcuff method (Natsume Seisakusho Co., Ltd., KN-210-1) at before and 1 h after p.o. (per oral) administration of the compounds. SHR were prewarmed at 50° C. for 3 to 5 min. in a warm box and placed into a restraining cage on heating plate (37° C.) for 5 to 15 min.

Table shows the % decrease of systolic blood pressure at 1 h after administration of the test compounds. Each value represents the mean of three animals.

TABLE

| Test Compound | Dosage (mg/kg) | Ratio of lowering blood pressure (%) |
| --- | --- | --- |
| (Present Compounds) | | |
| Compound of Example 1 | 1.0 | 43 |
| Compound of Example 1 | 0.3 | 11 |
| Compound of Example 8 | 1.0 | 54 |
| Compound of Example 8 | 0.3 | 43 |
| Compound of Example 9 | 1.0 | 56 |
| Compound of Example 9 | 0.3 | 46 |
| Compound of Example 11 | 1.0 | 54 |
| Compound of Example 11 | 0.3 | 37 |
| Compound of Example 20 | 1.0 | 52 |
| Compound of Example 20 | 0.3 | 22 |
| (Comparative Compounds) | | |
| BRL-34915 (see Formula A) | 1.0 | 28 |

TABLE-continued

| Test Compound | Dosage (mg/kg) | Ratio of lowering blood pressure (%) |
| --- | --- | --- |
| BRL-34915 (see Formula A) | 0.3 | 16 |

Acute toxicity test

Male ICR mice (6 weeks) were used. The test compounds (Examples 8 and 11) suspended in 0.5% methylcellulose solution were administered orally. These animals were examined for 7 days after administration. No mice which were administered each drug at the dose of 600 mg/kg were died (n=3). Both compounds showed low toxicity.

EXAMPLES (inclusive of reference and formulation examples)

The examples of the present invention are described in detail. However, the present invention is not limited thereto.

In the reference examples and the examples of the present invention, the signals of "NMR" and "MS" represent "nuclear magnetic resonance spectrum" and "mass spectrum", respectively.

REFERENCE EXAMPLE 1

7,8-dihydro-6,6-dimethyl-7,8-epoxy-6H-pyrano [2,3-f] benzo-2,1,3-oxadiazol 3-oxide

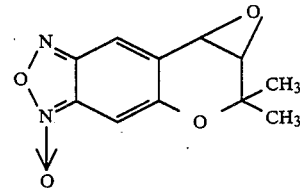

To a mixture of 4.41 g (18.9 m mol) of 6-amino-3,4-dihydro-2,2-dimethyl-3,4-epoxy-7-nitro-2H-benzo [b] pyran, 1.29 g (32 m mol) of sodium hydroxide, 400 ml of ethanol and 40 ml of water were added slowly dropwise 32.2 g (26 m mol) of 6% sodium hypochlorite solution at the room temperature with stirring.

After the completion of the reaction, the mixture solution was added with 1 l of saline solution and thrice extracted with ethyl acetate. The combined ethyl acetate layer was washed with saturated aqueous NaCl solution and dried over anhydrous sodium sulfate. After the solvent was distilled off, the residue was subjected to silica gel column chromatography using a developing solvent of ethyl acetate-hexane (1:2 (v/v)) to obtain 4.00 g (yield: 92%) of the intended compound. yellow crystals: m.p. 144° to 145° C.

REFERENCE EXAMPLE 2

7,8-dihydro-6,6-dimethyl-7,8-epoxy-6H-pyrano [2,3-f] benzo-2,1,3-oxadiazole

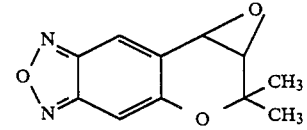

To a mixture of 1.00 g (4.27 m mol) of 7,8-dihydro-6,6-dimethyl-7,8-epoxy-6H-pyrano [2,3-f] benzo-2,1,3-oxadiazole 3-oxide and 6 ml of benzene was added dropwise 0.80 ml (4.70 m mol) of triethyl phosphite over 15 minutes at 60° C. under stirring. Then, the mixture was stirred for three hours. After the solvent was removed under the reduced pressure, the residue was subjected to a silica gel column chromatography using a developing solvent of ethyl acetate-hexane (1:1 (v/v)) to obtain 0.82 g of the intended compound (yield: 88%). A part of the obtained compound was recrystallized from hexane to obtain yellow crystals (m.p.: 97° to 99° C.).

REFERENCE EXAMPLE 3

7,8-dihydro-6,6-dimethyl-7hydroxy-8-amino-6H-pyrano [2,3-f] benzo-2,1,3-oxadiazole

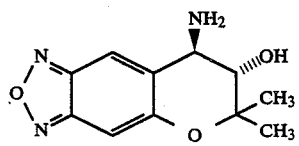

0.82 g of 7,8-dihydro-6,6-dimethyl-7,8-epoxy-6H-pyrano [2,3-f] benzo-2,1,3-oxadiazole (3.8 m mols) dissolved in 25 ml of 16.7% $NH_3$—EtOH solution was reacted in a pressure glass tube at 60° C. for 48 hours. The reaction solution was distilled off and the residue was subjected to a silica gel column chromatography using a developing solvent of ethyl acetate-methanol (5:1 (v/v)) to obtain 0.77 g (yield: 87%) of the intended compound as a brown solid. A part of the obtained compound was recrystallized from ethanol to obtain pure intended compound as colorless crystals.

m.p.: 223° to 225° C.

NMR ($CDCl_3$+DMSO-$d^6$) δ(ppm): 1.26(3H), 1.49(3H), 2.80–3.30(5H), 3.33(1H), 3.78(1H), 6.82(1H), 7.98(1H).

MS: 133(50%), 163(100%), 235($M^+$, 3%).

EXAMPLE 1

7,8-dihydro-6,6-dimethyl-7-hydroxy-8-methylureido-6H-pyrano [2,3-f] benzo-2,1,3-oxadiazole

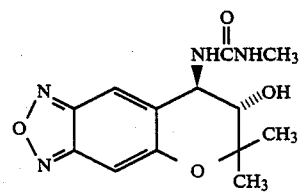

To a mixture of 200 mg (0.850 m mol) of 7,8-dihydro-6,6-dimethyl-7-hydroxy-8-amino-6H-pyrano [2,3-f] benzo-2,1,3-oxadiazole and 20 ml of dichloromethane were added 55 μl (0.935 m mol) of methyl isocyanate with stirring at the room temperature, followed by stirring for 23 hours.

The precipitated crystals were separated by filtration to obtain 227 mg (yield: 92%) of colorless crystals of the intended compound.

m.p.: 213°–215° C.

M.S.: 44, 202 (30%), 274 ($M^+$—$H_2O$, 6%).

EXAMPLE 2

7,8-dihydro-6,6-dimethyl-7-hydroxy-8-methylthioureido-6H-pyrano [2,3-f] benzo-2,1,3-oxadiazole

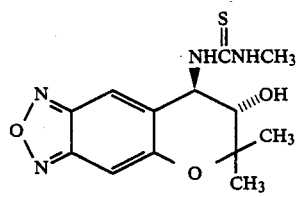

To a mixture of 200 mg (0.850 m mol) of 7,8-dihydro-6,6-dimethyl-7-hydroxy-8-amino-6H-pyrano [2,3-f] benzo-2,1,3-oxadiazole and 20 ml of dichloromethane were added 68 mg (0.935 m mol) of methylisothiocyanate with stirring at the room temperature, followed by stirring for 23 hours. The precipitated crystals were separated by filter to obtain 122 mg of the intended compound as colorless crystals. (yield: 47%)

m.p.: 213°–215° C.

MS: 91 (62%), 202 (67%), 290, 308 ($M^+$, 27%).

EXAMPLE 3

(Intermediate of the compound of the Example 3)

7,8-dihydro-6,6-dimethyl-7-hydroxy-8-(2-chloroethylureido)-6H-pyrano [2,3-f] benzo-2,1,3-oxadiazole

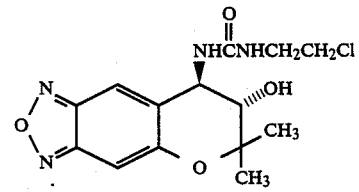

To a mixture of 400 mg (1.70 m mol) of 7,8-dihydro-6,6-dimethyl-7-hydroxy-8-amino-6H-pyrano [2,3-f] benzo-2,1,3-oxadiazole and 40 ml of dichloromethane were added 200 μl (1.87 m mol) of 2-chloroethyl isocyanate with stirring at the room temperature, followed by stirring for 6 hours. The precipitated crystals were separated by filter to obtain 480 mg (yield: 83%) of the intended compound as colorless crystals.

m.p.: 178°–180° C.

MS: 87 (57%), 163, 304 (78%), 340 ($M^+$, 8%).

(Compound of the Example 3)

7,8-dihydro-6,6-dimethyl-7-hydroxy-8-(2-oxo-imidazolidin-1-yl)-6H-pyrano [2,3-f] benzo-2,1,3-oxadiazole

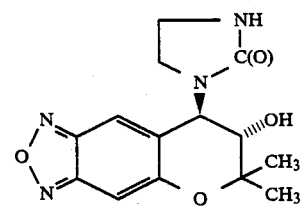

410 mg (1.2 m mol) of 7,8-dihydro-6,6-dimethyl-7-hydroxy-8-(2-chloroethylureido)-6H-pyrano [2,3-f] benzo-2,1,3-oxadiazole obtained above were added with 3.32 g (24 m mol) of potassium carbonate, 400 mg (2.4 m mol) of potassium iodide and 50 ml of absolute acetone and the mixture was refluxed for 13 hours under a nitrogen atmosphere. At the room temperature, the impurities were filtered off. After the filtrate was distilled off, the residue was added with ethyl acetate, washed with water and saturated aqueous NaCl solution and dried over anhydrous magnesium sulfate. Then, the solvent was distilled off. The residue was recrystallized from ethyl acetate to obtain 102 mg (yield: 34%) of the pure intended compound as colorless crystals.

EXAMPLE 4

7,8-dihydro-6,6-dimethyl-7-hydroxy-8-isopropylureido-6H-pyrano [2,3-f] benzo-2,1,3-oxadiazole

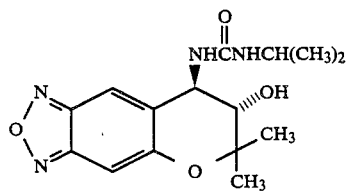

To a mixture of 200 mg (0.850 m mol) of 7,8-dihydro-6,6-dimethyl-7-hydroxy-8-amino-6H-pyrano [2,3-f] benzo-2,1,3-oxadiazole and 20 ml of dichloromethane were added 92 μl (0.935 m mol) of isopropyl isocyanate with stirring at the room temperature, followed by stirring for 6 hours. The precipitated crystals were filtered off to obtain 120 mg (yield: 44%) of the intended compounds as colorless crystals.

m.p.: 201°–203° C.

MS: 43 (40%), 202, 302 (20%), 320 (M+. 12%).

EXAMPLE 5

(Intermediate of the compound of the Example 5)

7,8-dihydro-6,6-dimethyl-7-hydroxy-8-(2-chloroethoxycarbonylamino)-6H-pyrano [2,3-f] benzo-2,1,3-oxazole

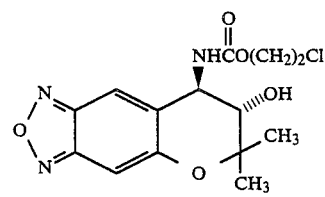

To a mixture of 400 mg (1.70 m mol) of 7,8-dihydro-6,6-dimethyl-7-hydroxy-8-amino-6H-pyrano [2,3-f] benzo-2,1,3-oxadiazole, 260 μl (1.87 m mol) of triethylamine and 40 mg of dichloromethane were added 193 μl (1.87 m mol) of 2-chloroethyl chloroformate stirred at the room temperature, followed by stirring for 21 hours. The reaction solution was thrice washed with water and dried over anhydrous sodium sulfate. After the solvent was distilled off, the residue was recrystallized from chloroform to obtain 507 mg (yield: 87%) of the intended compound as pale yellow crystals.

m.p.: 164°–166° C.

MS: 133 (48%), 235, 307 (M+, 25%).

(COMPOUND OF EXAMPLE 5)

7,8-dihydro-6,6-dimethyl-7-hydroxy-8-(2-oxoxazolin-3-yl)-6H-pyrano [2,3-f] benzo-2,1,3-oxadiazole

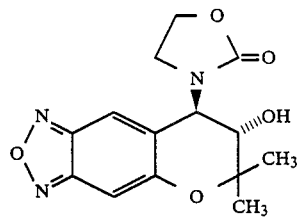

400 mg (1.17 m mol) of 7,8-dihydro-6,6-dimethyl-7-hydroxy-8-(2-chloroethoxycarbonylamino)-6H-pyrano [2,3-f] benzo-2,1,3-oxadiazole obtained above were added with 3.24 g (23.4 m mol) of potassium carbonate, 388 mg (2.34 m mol) of potassium iodide and 50 ml of absolute acetone and the mixture was heated to reflux for 26 hours under a nitrogen atmosphere. At the room temperature, the insoluble matters were filtered off. The filtrate was added with ethyl acetate, washed thrice with water and dried over anhydrous magnesium sulfate. Then, the solvent was distilled off. The residue was subjected to a silica gel column chromatography using a developing solvent of ethyl acetate-methanol (10:1 (v/v)) to obtain 339 mg (yield: 94%) of the intended compound as brown solid. A part of the obtained compound was recrystallized from ethyl acetate to obtain yellow crystals.

m.p.: 177.5°–180° C.

MS: 43 (25%), 272, 287 (65%), 305 (M+. 8%).

EXAMPLE 6

(Intermediate of the compound of Example 6)

7,8-dihydro-6,6-dimethyl-7-hydroxy-8-(1-piperidinyl)-6H-pyrano [2,3-f] benzo-2,1,3-oxadiazole 3-oxide

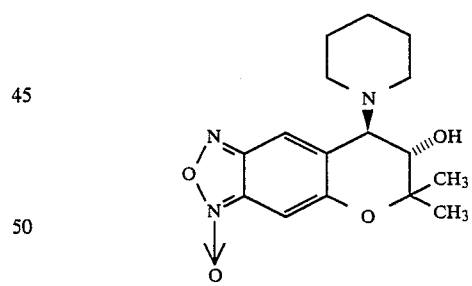

To a mixture of 924 mg (2.88 m mol) of 3,4-dihydro-2,2-dimethyl-3-hydroxy-4-(1-piperidinyl)-6-amino-7-nitro-2H-benzo [b] pyran, 0.7 ml of 50% aqueous potassium hydroxide solution, 4 ml of CH₂Cl₂ and 10 mg of Bu₄N⁺Br⁻ were added 4.97 g (4.03 m mol) of 6% aqueous NaOCl solution with stirring at the room temperature and reacted for 9 hours. The organic layer was separated and water layer was twice extracted with methylene chloride. The combined methylene chloride layer was washed with water, dried over anhydrous sodium sulfate and the solvent was distilled off. The residue was subjected to a silica gel column chromatography using a developing solvent of ethyl acetate-hexane (1:3 (v/v)) to obtain 297 mg (yield: 43%) of the intended compound as oil. A part of the obtained compound was dissolved in ethanol and added with HCl—EtOH and dry ether to obtain hydrochloride of the intended compound as yellow crystals.

m.p.: 210°–213° C.

(COMPOUND OF EXAMPLE 6)

7,8-dihydro-6,6-dimethyl-7-hydroxy-8-(1-piperidinyl)-6H-pyrano [2,3-f] benzo-2,1,3-oxadiazole

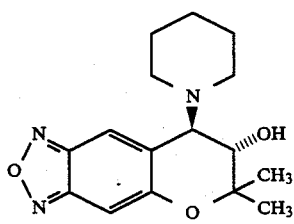

A mixture of 297 mg (0.93 m mol) of 7,8-dihydro-6,6-dimethyl-7-hydroxy-8-(1-piperidinyl)-6H-pyrano [2,3-f] benzo-2,1,3-oxadiazole 3-oxide, 6 ml of ethylene glycol and 60 mg (0.93 m mol) of NaN₃ was heated to 140° C. and reacted for 1.2 hours. After cooling, the reaction solution was poured into water and extracted thrice with chloroform. After the combined chloroform layer was dried over anhydrous sodium sulfate, the solvent was distilled off. The residue was subjected to a silica gel column chromatography using a developing solvent of ethyl acetate-hexane (1:3 (v/v)) to obtain 84 mg (yield: 30%) of the intended compound as oil. A part of the obtained compound was dissolved in ethanol-ethyl ether and added with HCl—EtOH to obtain the hydrochloride of the intended compound as pale yellow crystals.

m.p.: 202°–205° C.

EXAMPLE 7

(Intermediate of the compounds of Examples 7 and 8)

7,8-dihydro-6,6-dimethyl-7-hydroxy-8-(n-(1-oxo-4-chloro) butyl)amino-6H-pyrano [2,3-f] benzo-2,1,3-oxadiazole

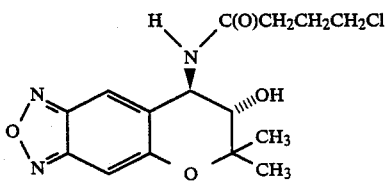

To a mixture of 80 mg (0.34 m mol) of 7,8-dihydro-6,6-dimethyl-7-hydroxy-8-amino-6H-pyrano [2,3-f] benzo-2,1,3-oxadiazole, 14 mg (0.374 m mol) of sodium hydroxide, 6 ml of methylene chloride and 3 ml of water were added 42 μl (0.374 m mol) of 4-chlorobutylyl chloride with stirring at the room temperature, followed by stirring for 30 minutes. After the completion of the reaction, the methylene chloride layer was separated off and the water layer was extracted twice with methylene chloride. The combined methylene chloride was washed with diluted aqueous sodium bicarbonate, water and saturated aqueous NaCl solution in the order named and dried over anhydrous magnesium sulfate. After the solvent was distilled off, the residue was subjected to a preparative silica gel thin layer chromatography using a developing solvent of ethyl acetate-methanol (10:1 (v/v)) to obtain 194 mg (yield: 37%) of the intended compound.

pale yellow crystals: m.p.: 160°–161° C.

(COMPOUND OF EXAMPLE 7)

6,6-dimethyl-8-(2-oxo-1-pyrrolydinyl)-6H-pyrano [2,3-f] benzo-2,1,3-oxadiazole

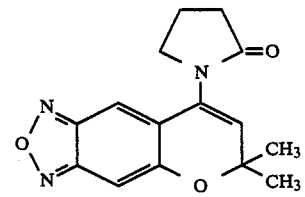

A mixture of 116 mg of 7,8-dihydro-6,6-dimethyl-7-hydroxy-8-(n-(1-oxo-4-chloro)butyl)amino-6H-pyrano [2,3-f] benzo-2,1,3-oxadiazole, 940 mg of potassium carbonate and 113 mg of potassium iodide was suspended in 20 ml of acetone and refluxed under a nitrogen atmosphere for 24 hours. After cooling, impurities were filtered off with suction and removed, and the solvent was distilled off. The residue was subjected to a silica gel column chromatography using a developing solvent of ethyl acetate-methanol (5:1 (v/v)) to obtain the objective compound. The obtained compound was recrystallized from ethanol to obtain 72 mg (yield: 74%) of the pure intended compound as colorless crystals.

m.p.: 238°–240° C.

EXAMPLE 8

7,8-dihydro-6,6-dimethyl-7-hydroxy-8-(2-oxo-1-pyrrolidinyl)-6H-pyrano [2,3-f] benzo-2,1,3-oxadiazole

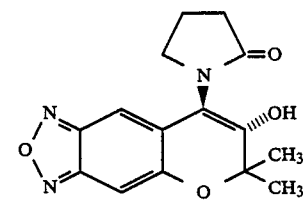

A mixture of 150 mg (0.441 m mol) of 7,8-dihydro-6,6-dimethyl-7-hydroxy-8-(n-(1-oxo-4-chloro)butyl)amino-6H-pyrano [2,3-f] benzo-2,1,3-oxadiazole, 1.22 g (8.83 m mol) of potassium carbonate and 146 mg (0.882 m mol) of potassium iodide was suspended in 20 ml acetone and refluxed under a nitrogen atmosphere for 17 hours. After cooling, insoluble matters was filtered off. Then, the filtrate was diluted with ethyl acetate and washed thrice with water. After the obtained product was dried over anhydrous sodium sulfate and the solvent was concentrated to obtain 33 mg (yield: 25%) of the intended compound as colorless crystals.

m.p.: 242°–244° C.

NMR (CDCl₃+DMSO-d⁶) δ(ppm): 1.35(3H), 1.54(3H), 1.94–2.73(4H), 3.05–3.61(3H), 3.77(1H), 5.33(1H), 6.97(1H), 7.39(1H).

MS: 86(100%), 270(95%), 285(60%), 303(M⁺, 12%).

EXAMPLE 9

(Intermediate of the compound of Example 9)

7,8-dihydro-6,6-dimethyl-7-hydroxy-8-(n-(1-oxo-5-chloro) pentyl)amino-6H-pyrano [2,3-f] benzo-2,1,3-oxadiazole

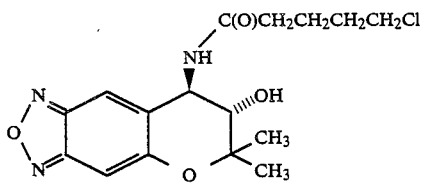

200 mg (0.85 m mol) of 7,8-dihydro-6,6-dimethyl-7-hydroxy-8-amino-6H-pyrano [2,3-f] benzo-2,1,3-oxadiazole and 37 mg (0.94 m mol) of sodium hydroxide were dissolved in a mixture solution of 10 ml of chloroform and 5 ml of water and added with 120 μl (0.94 m mol) of 5-chlorovaleryl chloride. After the mixture solution was stirred for 15 minutes, the chloroform layer was separated and the water layer was twice extracted with chloroform. The combined chloroform layer was washed with saturated sodium bicarbonate and dried over anhydrous sodium sulfate. The solvent was distilled off and the residue was subjected to a preparative gel column chromatography using a developing solvent of ethyl acetate:methanol (0.1 (v/v) to obtain 56 mg of the intended compound as crystals. (yield: 16%). The obtained compound was arranged to be a starting material of the Example 9, without any further purification.

(COMPOUND OF EXAMPLE 9)

7,8-dihydro-6,6-dimethyl-7-hydroxy-8-(2-oxo-1-piperidinyl)-6H-pyrano [2,3-f] benzo-2,1,3-oxadiazole

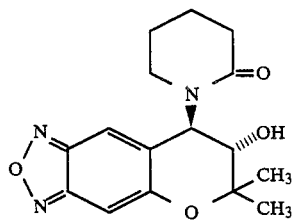

A mixture of 56 mg of 7,8-dihydro-6,6-dimethyl-7-hydroxy-8-(n-(1-oxo-5-chloro)pentyl)amino-6H-pyrano [2,3-f] benzo-2,1,3-oxadiazole, 440 mg (3.16 m mol) of potassium carbonate and 52 mg (0.316 m mol) of potassium iodide was suspended in 10 ml of acetone and refluxed under a nitrogen atmosphere for 22 hours. After cooling, insoluble matters were removed by filtration and the filtrate was diluted with ethyl acetate. The obtained solution was washed twice with water and once with saturated aqueous NaCl solution and then, dried over anhydrous sodium sulfate. After the solvent was distilled off, the residue was subjected to a preparative silica gel thin layer chromatography using a developing solvent of ethyl acetate-methanol (10:1 (v/v)) to obtain 30 mg (yield: 54%) of the intended compound. A part of the obtained compound was recrystallized from a mixed solvent of ethyl acetate-hexane to obtain pale yellow crystals.

m.p.: 192°–194° C.

EXAMPLE 10

7,8-dihydro-6,6-dimethyl-7-hydroxy-8-pyrrolidino-6H-pyrano [2,3-f] benzo-2,1,3-oxadiazole

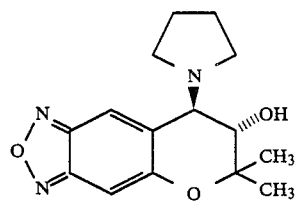

A mixture of 150 mg (0.687 m mol) of 7,8-dihydro-6,6-dimethyl-7,8-epoxy-6H-pyrano [2,3-f] benzo-2,1,3-oxadiazole, 63 μl (0.756 m mol) of pyrrolidine and 2 ml of ethanol was refluxed with stirring for 31 hours. After the solvent was distilled off, the residue was subjected to a preparative silica gel thin layer chromatography using a developing solvent of ethyl acetate-methanol (1:1 (v/v)) to obtain 120 mg (yield: 60%) of the intended compound. A part of the obtained compound was dissolved in dry ether and added with HCl—EtOH to obtain hydrochloride of the intended compound as pale yellow crystals.

m.p.: 208°–209° C.

EXAMPLE 11

7,8-dihydro-6,6-dimethyl-7-hydroxy-8-acetylamino-6H-pyrano [2,3-f] benzo-2,1,3-oxadiazole

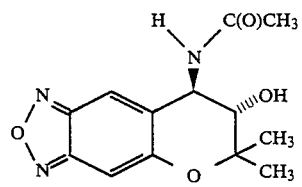

To a mixture of 200 mg (0.850 m mol) of 7,8-dihydro-6,6-dimethyl-7-hydroxy-8-amino-6H-pyrano [2,3-f] benzo-2,1,3-oxadiazole, 128 μl (0.917 m mol) of triethylamine and 17 ml of methylene chloride were added 128 μl (0.917 m mol) of acetyl chloride with stirring at 0° C., followed by stirring for 30 minutes. After the completion of the reaction, the precipitated crystals were filtered. The crystals were washed successively with methylene chloride and water and dried at 80° C. under reduced pressure to obtain 223 mg (yield: 88%) of the intended compound.

Further, after the filtrate was washed thrice with water and dried over anhydrous sodium sulfate, the solvent was distilled off. The residue was recrystallized from ethyl acetate to obtain 7 mg of the intended compound as pale yellow needlelike crystals.

m.p.: 241.0°–242.0° C.

EXAMPLE 12

7,8-dihydro-6,6-dimethyl-7-hydroxy-8-chloroacetylamino-6H-pyrano [2,3-f] benzo-2,1,3-oxadiazole

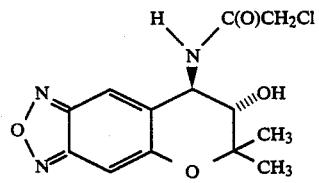

A mixture of 200 mg (0.85 m mol) of 7,8-dihydro-6,6-dimethyl-7-hydroxy-8-amino-6H-pyrano [2,3-f] benzo-2,1,3-oxadiazole, 130 μl (0.935 m mol) of triethylamine and 20 ml of methylene chloride was added with 74 μl (0.935 m mol) of chloroacetyl chloride with stirring at the room temperature, followed by further stirring for 30 minutes. After the completion of the reaction, the precipitated crystals were separated by filtration to obtain 201 mg (yield: 76%) of the intended compound.

Colorless crystals: m.p.: 232.0°–234.0° C.

EXAMPLE 13

7,8-dihydro-6,6-dimethyl-7-hydroxy-8-pivaloylamino-6H-pyrano [2,3-f] benzo-2,1,3-oxadiazole

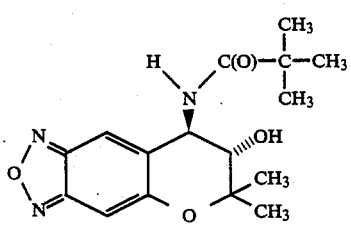

To a mixture of 200 mg (0.85 m mol) of 7,8-dihydro-6,6-dimethyl-7-hydroxy-8-amino-6H-pyrano [2,3-f] benzo-2,1,3-oxadiazole, 130 μl (0.935 m mol) of triethylamine and 20 ml of methylene chloride were added 115 μl (0.935 m mol) of pivaloyl chloride (trimethylacetyl chloride) with stirring at the room temperature, followed by further stirring for 3.5 hours. After the completion of the reaction, the mixture solution was washed thrice with water and dried over anhydrous magnesium sulfate. After the solvent was distilled off, the residue was recrystallized from ethanol to obtain the pure intended compound. (yield: 191 mg, yield: 70%).

Pale yellow crystal: m.p.: 213.0°–214.0° C.

EXAMPLE 14

7,8-dihydro-6,6-dimethyl-7-hydroxy-8-isobutyrylamino-6H-pyrano [2,3-f] benzo-2,1,3-oxadiazole

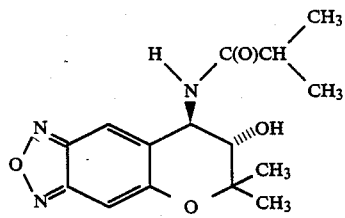

To a mixture of 200 mg (0.85 m mol) of 7,8-dihydro-6,6-dimethyl-7-hydroxy-8-amino-6H-pyrano [2,3-f] benzo-2,1,3-oxadiazole, 130 μl (0.935 m mol) of triethyl amine and 20 ml of dichloromethane were added 98 μl (0.935 m mol) of isobutyryl chloride with stirring at the room temperature, followed by further stirring for four hours. After the completion of the reaction, the mixture was washed thrice with water and dried over anhydrous magnesium sulfate. After the solvent was distilled off, the residue was recrystallized from ethanol to obtain 109 mg (yield: 42%) of the pure intended compound.

Pale yellow crystal: m.p.: 194.0°–196.5° C.

EXAMPLE 15

7,8-dihydro-6,6-dimethyl-7-hydroxy-8-trifluoroacetyl amino-6H-pyrano [2,3-f] benzo-2,1,3-oxadiazole

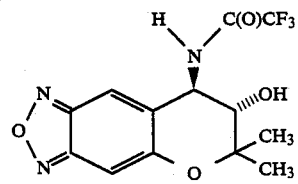

A mixture of 300 mg (1.28 m mol) of 7,8-dihydro-6,6-dimethyl-7-hydroxy-8-amino-6H-pyrano [2,3-f] benzo-2,1,3-oxadiazole and 3 ml of pyridine were added with 180 μl (1.28 m mol) of anhydrous trifluoroacetic acid with stirring for 3 hours at 0° C., followed by further stirring for 3 hours at the room temperature. After the completion of the reaction, the mixture was washed thrice with water and dried over anhydrous sodium sulfate. After the solvent was distilled off, the residue was subjected to a silica gel column chromatography using a developing solvent of ethyl acetate-methanol (10:1 (v/v)) to obtain 124 mg (yield: 29%) of the intended compound. A part of the obtained compound was recrystallized from ethanol to obtain the pure intended compound.

Pale yellow crystal: m.p.: 257.0°–259.0° C.

EXAMPLE 16

7,8-dihydro-6,6-dimethyl-7-hydroxy-8-propionylamino-6H-pyrano [2,3-f] benzo-2,1,3-oxadiazole

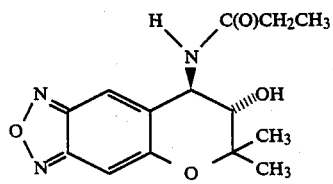

To a mixture of 200 mg (0.85 m mol) of 7,8-dihydro-6,6-dimethyl-7-hydroxy-8-amino-6H-pyrano [2,3-f] benzo-2,1,3-oxadiazole, 130 ml (0.935 m mol) of triethylamine and 20 ml of methylene chloride were added 81 μl (0.935 m mol) of propionyl chloride with stirring at the room temperature, followed by further stirring for 6 hours. After the completion of the reaction, the mixture solution was washed thrice with water and dried over anhydrous magnesium sulfate. After the solvent was distilled off, the residue was recrystallized from ethanol to obtain 77 mg (yield: 31%) of the pure intended compound.

Pale yellow crystal: m.p.: 203.0°–205.0° C.

EXAMPLE 17

7,8-dihydro-6,6-dimethyl-7-hydroxy-8-bromoacetylamino-6H-pyrano [2,3-f] benzo-2,1,3-oxadiazole

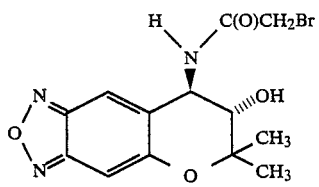

To a mixture of 180 mg (0.765 m mol) of 7,8-dihydro-6,6-dimethyl-7-hydroxy-8-amino-6H-pyrano [2,3-f] benzo-2,1,3-oxadiazole, 117 μl (0.842 m mol) of triethylamine and 20 ml of methylene chloride were added 73 μl (0.842 m mol) of bromoacetyl chloride with stirring at the room temperature, followed by further stirring for 1 hour. After the completion of the reaction, the precipitated crystal was filtered to obtain 199 mg of the intended compound. (yield: 73%).

Colorless crystal: m.p.: 214.0°–271.0° C.

EXAMPLE 18

7,8-dihydro-6,6-dimethyl-7-acetoxy-8-acetylamino-6H-pyrano [2,3-f] benzo-2,1,3-oxadiazole

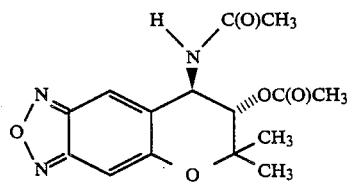

A mixture of 100 mg (0.36 m mol) of 7,8-dihydro-6,6-dimethyl-7-hydroxy-8-acetylamino-6H-pyrano [2,3-f] benzo-2,1,3-oxadiazole, 2 ml of pyridine and 34 μl (0.36 m mol) of acetic anhydride was stirred at the room temperature for 24 hours. After the completion of the reaction, the mixture was diluted with ethyl acetate, washed with water and saturated anhydrous NaCl solution and dried over anhydrous magnesium sulfate. After the solvent was distilled off, the residue was recrystallized from chloroform to obtain 58 mg (yield: 26%) of the intended compound.

Pale yellow crystal: m.p.: 236.0°–238.5° C.

EXAMPLE 19

6,6-dimethyl-8-acetylamino-6H-pyrano [2,3-f] benzo-2,1,3-oxadiazole

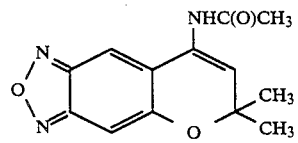

To a mixture of 80 mg (0.289 m mol) of 7,8-dihydro-6,6-dimethyl-7-hydroxy-8-acetylamino-6H-pyrano [2,3-f] benzo-2,1,3-oxadiazole and 5 ml of dried tetrahydrofuran were added 25 mg of sodium hydride (oil, content of more than 55%) with stirring for 1 hour at the room temperature. After the mixture was carefully added with water and extracted thrice with ethyl acetate. The combined ethyl acetate layer was washed successively with 0.5N hydrochloric acid, water and saturated aqueous NaCl solution and dried over anhydrous magnesium sulfate. After the solvent was distilled off, the residue was subjected to a preparative thin layer column chromatography using a developing solvent of ethyl acetate-methanol (10:1 (v/v)) to obtain 24 mg (yield: 32%) of the intended compound. The obtained compound was recrystallized from ethanol to obtain the pure intended compound.

m.p.: 218.0°–220.0° C.

EXAMPLE 20

(Intermediate compound 1 of the compound of Example 20)

7,8-dihydro-6,6-dimethyl-7-hydroxy-8-hydrazino-6H-pyrano [2,3-f] benzo-2,1,3-oxadiazole

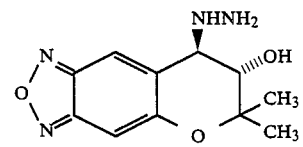

To 1.0 g of 7,8-dihydro-6,6-dimethyl-7,8-epoxy-6H-pyrano [2,3-f] benzo-2,1,3-oxadiazole were added 10 ml of ethanol and 250 mg of hydrazine-hydrate and heated to reflux for 16 hours. The solvent was distilled off under reduced pressure and added with ethyl acetate. The precipitated crystals were filtered to obtain intermediate compound 1 as pale yellow crystals. (Yield: 1.0 g, yield: 89%).

m.p.: 126.0°–127.0° C.

(Intermediate compound 2 of the compound of Example 20)

7,8-dihydro-6,6-dimethyl-7-hydroxy-8,2-(2-hydroxycarbonylethyl) hydrazino-6H-pyrano [2,3-f] benzo-2,1,3-oxadiazole

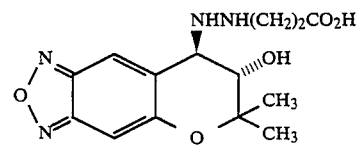

To 1.0 g of 7,8-dihydro-6,6-dimethyl-7-hydroxy-8-hydrazino-6H-pyrano [2,3-f] benzo-2,1,3-oxadiazole were added 10 ml of ethanol and 300 mg of ethyl acrylate and heated to reflux for 3 hours. The solvent was distilled off under reduced pressure and the residue was added with 10 ml of ethanol and 3 ml of 1N sodium hydroxide solution and stirred at the room temperature for 1 hour. The reaction solution was adjusted its pH to 2–3 by adding 5% hydrochloric acid and extracted with chloroform. The chloroform layer was dried over anhydrous sodium sulfate and the solvent was distilled off. The residue was added with chloroformethyl acetate solution (1:1 (v/v)) and the precipitated crystals were filtered to obtain intermediate compound 2 as pale yellow crystals. (Yield: 250 mg, yield: 20%).

(Intermediate compound 3 of the compound of Example 20)

7,8-dihydro-6,6-dimethyl-7-hydroxy-8-(1-tert-butoxycarbonyl-3-oxo-pyrazolidin-2yl)-6H-pyrano [2,3-f] benzo-2,1,3-oxadiazole

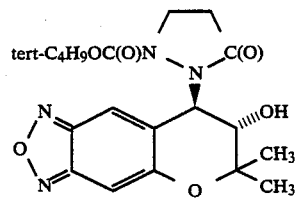

To a mixture of 250 mg of 7,8-dihydro-6,6-dimethyl-7-hydroxy-8-2-(2-hydroxycarbonylethyl)hydrazino-6H-pyrano [2,3-f] benzo-2,1,3-oxadiazole, 10 ml of chloroform and 100 mg of triethylamine were added 200 mg of di-tert-butyldicarbonate with stirring for 1 hour at the room temperature. The mixture was added with 20 ml of saturated aqueous ammonium chloride solution and extracted with chloroform. The chloroform layer was dried over anhydrous sodium sulfate and the solvent was distilled off. The residue was added with 2 ml of acetic anhydride and 100 mg of anhydrous sodium acetate and heated at 60° C. for 10 minutes. The solvent was distilled off and added with 30 ml of water and extracted with chloroform. The chloroform layer was dried over anhydrous sodium sulfate and the solvent was distilled off. The residue was added with ethyl acetate-diethyl ether (1:1 (v/v)) and the precipitated crystals were filtered to obtain intermediate compound 3 as pale yellow crystals. (Yield: 200 mg, yield: 65%) m.p.: 190°–191.0° C.

(COMPOUND OF EXAMPLE 20)

7,8-dihydro-6,6-dimethyl-7-hydroxy-8-(3-oxo-pyrazolidin-2-yl)-6H-pyrano [2,3-f] benzo-2,1,3-oxadiazole

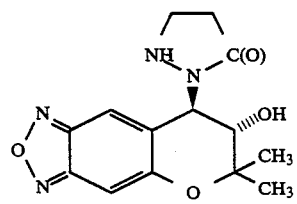

To 200 mg of 7,8-dihydro-6,6-dimethyl-7-hydroxy-8-(1-tert-butoxycarbonyl-3-oxo-pyrazolidin-2-yl)-6H-pyrano [2,3-f] benzo-2,1,3-oxadiazole were added 2 ml of trifluoroacetic acid under ice-cooling and stirred for 1 hour at the room temperature. The obtained solution was neutralized with saturated sodium bicarbonate solution and extracted with chloroform. The chloroform layer was dried over anhydrous sodium sulfate and the solvent was distilled off. The residue was added with ethyl acetate-diethyl ether (1:1) and the precipitated crystals were filtered to obtain the intended compound as colorless crystals. (Yield: 130 mg, yield: 84%) m.p.: 230.0°–233.0° C.

FORMULATION EXAMPLE 1

| Tablets | |
|---|---|
| Compound of Example 8 | 10 g |
| Lactose | 260 g |
| Crystal celluoose powder | 600 g |
| Corn starch | 350 g |
| Hydroxypropyl cellulose | 100 g |
| CMC-Ca* | 150 g |
| Magnesium stearate | 30 g |
| Total | 1,500 g |

(*carboxymethylcellulose calcium)

The above components were mixed by a usual method and then tabletted to produce 10,000 tablets each containing 1 mg of the active ingredient.

FORMULATION EXAMPLE 2

| Capsules | |
|---|---|
| Compound of Example 8 | 10 g |
| Lactose | 440 g |
| Crystal cellulose powder | 1,000 g |
| Magnesium stearate | 50 g |
| Total | 1,500 g |

The above components were mixed by a usual method and then packed in gelatin capsules to obtain 10,000 capsules each containing 1 mg of the active ingredient.

FORMULATION EXAMPLE 3

| Soft capsules | |
|---|---|
| Compound of Example 8 | 10 g |
| PEG (polyethylene glycol) 400 | 479 g |
| Saturated fatty acid triglyceride | 1,500 g |
| Peppermint oil | 1 g |
| Polysorbate 80 | 10 g |
| Total | 2,000 g |

The above components were mixed and packed in No. 3 soft gelatin capsules by a usual method to obtain 10,000 soft capsules each containing 1 mg of the active ingredient.

FORMULATION EXAMPLE 4

| Ointment | |
|---|---|
| Compound of Example 8 | 1.0 g |
| Liquid paraffin | 10.0 g |
| Cetanol | 20.0 g |
| White vaseline | 68.4 g |
| Ethylparaben | 0.1 g |
| L-menthol | 0.5 g |
| Total | 100.0 g |

The above components were mixed by a usual method to obtain a 1% ointment.

FORMULATION EXAMPLE 5

| Suppository | |
|---|---|
| Compound of Example 8 | 1 g |
| Witepsol H15* | 478 g |
| Witepsol W35* | 520 g |
| Polysorbate 80 | 1 g |

-continued

| Suppository | |
|---|---|
| Total | 1,000 g |

(*Trademark for triglyceride compound)

The above components were melt-mixed by a usual method and poured into suppository containers, followed by cooling for solidification to obtain 1,000 suppositories of 1 g each containing 1 mg of the active component.

FORMULATION EXAMPLE 6

| Injection formulation | |
|---|---|
| Compound of Example 8 | 1 mg |
| Distilled water for injection formulation | 50 ml |

The formulation is prepared by dissolving the compound in the distilled water whenever it is required.

What is claimed is:

1. A compounds of the formula (I):

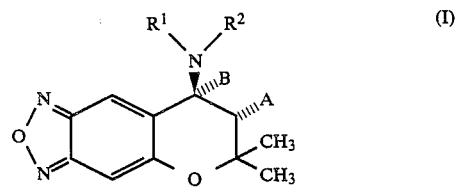

wherein

A represents OH or $OC(O)CH_{3-n}X_n$ in which X represents fluorine atom, chlorine atom, bromine atom, a methyl group or a methoxy group and n represents 0 or an integer of 1 to 3, or A and B together represents a bond;

B represents hydrogen atom or a bond together with A;

when $R^1$ represents hydrogen atom, $R^2$ represents hydrogen atom, $C(Z)CH_{3-n}X_n$ or $C(Z)NHCH_{3-n}X_n$ in which Z represents oxygen atom or sulfur atom and X has the same meaning as defined above;

when $R^1$ does not represent hydrogen atom, $R^1$ and $R^2$ together represents $(CH_2)_m$, $(CH_2)_{m-}C(Z)$, $N(R^3)(CH_2)_2C(Z)$, $(CH_2)_{m-2}NHC(Z)$ or $(CH_2)_{m-2}OC(Z)$ in which m represents an integer of 4 or 5, $R^3$ represents hydrogen atom or a methyl group and Z has the same meaning as defined above, or pharmacological acceptable salts of the compounds which can form salts.

2. A compound as claimed in claim 1 wherein when $R^1$ represents hydrogen atom, $R^2$ represents $C(Z)CH_{3-n}X_n$ or $C(Z)NHCH_{3-n}X_n$.

3. A compound as claimed in claim 1, wherein A represents OH.

4. A compound as claimed in claim 3, wherein $R^1$ represents hydrogen atom and $R^2$ represents $C(O)CH_3$ or $C(O)NHCH_3$.

5. A compound as claimed in claim 3, wherein $R^1$ represents hydrogen atom and $R^2$ represents $C(O)CH_3$.

6. A compound as claimed in claim 3, wherein $R^1$ and $R^2$ together represent $(CH_2)m-1C(O)$.

7. A compound as claimed in claim 3, wherein $R^1$ and $R^2$ together represent $(CH_2)_3C(O)$.

8. A compound as claimed in claim 3, wherein $R_1$ and $R^2$ together represent $(CH_2)_4C(O)$.

9. A compound as claimed in claim 3, wherein $R^1$ and $R^2$ together represent $N(R^3)(CH_2)_2C(O)$, $(CH_2)_2NHC(O)$ or $(CH_2)_2OC(O)$.

10. A compound as claimed in claim 1, wherein $R^1$ and $R^2$ simultaneously represent hydrogen atom and A represents OH.

11. An antihypertensive, coronary or cerebral vasodilator or anti-asthma composition comprising:
 (a) an antihypertensive, coronary or cerebral vasodilator or anti-asthma effective amount of the compound of Claim 2, and
 (b) a pharmaceutically acceptable diluent or carrier.

12. A method of treating hypertension in a subject in need of such treatment comprising administering to the subject an antihypertensive effective amount of the compound of claim 2, to produce such effect.

13. A method of treating cardiovascular disorder in a subject in need of such treatment comprising administering to the subject a coronary vasodilating effective amount of the compound of claim 2, to produce such effect.

14. A method of treating cerebrovascular disorder in a subject in need of such treatment comprising administering to the subject a cerebral vasodilating effective amount of the compound of claim 2, to produce such effect.

15. A method of treating asthma in a subject in need of such treatment comprising administering to the subject an anti-asthma effective amount of the compound of claim 2, to produce such effect.

* * * * *

UNITED STATES PATENT AND TRADEMARK OFFICE
CERTIFICATE OF CORRECTION

PATENT NO. : 4,900,752

DATED : February 13, 1990

INVENTOR(S) : K. Seto, H. Matsumoto, Y. Kamikawaji, K. Ohrai, K. Nakayama, R. Sakoda and Y. Masuda It is certified that error appears in the above-identified patent and that said Letters Patent is hereby corrected as shown below:

Column 19, line 30, change "(0.1" to --(10:1--.

Column 27, line 47 (claim 1), change "$(CH_2)_m C(Z)$" to --$(CH_2)_{m-1} C(Z)$--.

Column 28, line 15 (claim 6), change "$(CH_2)m-1 C(O)$" to --$(CH_2)_{m-1} C(O)$--.

Signed and Sealed this

Fourth Day of June, 1991

Attest:

HARRY F. MANBECK, JR.

*Attesting Officer*     *Commissioner of Patents and Trademarks*

UNITED STATES PATENT AND TRADEMARK OFFICE
CERTIFICATE OF CORRECTION

PATENT NO. : 4,900,752

DATED : February 13, 1990

INVENTOR(S) : Kiyotomo SETO et al.

It is certified that error appears in the above-identified patent and that said Letters Patent is hereby corrected as shown below: Column 18, lines 40-49, Change " 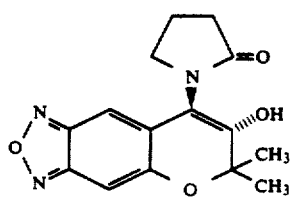 "

to -- 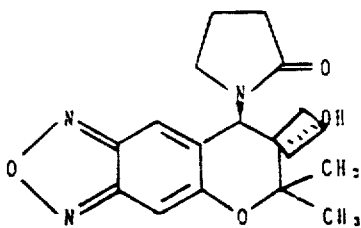 --

Signed and Sealed this

Eighth Day of September, 1992

*Attest:*

DOUGLAS B. COMER

*Attesting Officer*   *Acting Commissioner of Patents and Trademarks*